United States Patent
Villani et al.

(10) Patent No.: US 6,864,374 B2
(45) Date of Patent: Mar. 8, 2005

(54) SYNTHESIS OF R(+)α-LIPOIC ACID

(75) Inventors: Flavio Villani, Parma (IT); Antonio Nardi, Paderno Dugnano (IT); Annibale Salvi, Milan (IT); Giovanna Falabella, Milan (IT)

(73) Assignee: Laboratorio Chimico Internazionale S.p.A., Milan (IT)

(*) Notice: Subject to any disclaimer, the term of this patent is extended or adjusted under 35 U.S.C. 154(b) by 168 days.

(21) Appl. No.: 10/398,890

(22) PCT Filed: Oct. 8, 2001

(86) PCT No.: PCT/EP01/11576

§ 371 (c)(1),
(2), (4) Date: Apr. 9, 2003

(87) PCT Pub. No.: WO02/30919

PCT Pub. Date: Apr. 18, 2002

(65) Prior Publication Data

US 2004/0002610 A1 Jan. 1, 2004

(30) Foreign Application Priority Data

Oct. 10, 2000 (IT) ........................ MI200A2188

(51) Int. Cl.$^7$ ............................ C07D 339/02
(52) U.S. Cl. ...................................... 549/39
(58) Field of Search ............................ 549/39; 514/440

(56) References Cited

U.S. PATENT DOCUMENTS

| | | | |
|---|---|---|---|
| 4,772,727 A | | 9/1988 | Sutherland et al. |
| 5,281,722 A | | 1/1994 | Blaschke et al. |
| 5,705,192 A | * | 1/1998 | Bethge et al. ............... 424/489 |
| 6,140,512 A | * | 10/2000 | Adger et al. ................... 549/39 |
| 6,313,164 B1 | * | 11/2001 | Fujita et al. ................. 514/440 |
| 6,331,559 B1 | * | 12/2001 | Bingham et al. ............ 514/440 |
| 6,462,202 B1 | * | 10/2002 | Schuhbauer et al. ........... 549/39 |
| 6,605,637 B1 | * | 8/2003 | Harnett et al. .............. 514/440 |
| 6,670,484 B2 | * | 12/2003 | Villani et al. .................. 549/39 |

* cited by examiner

*Primary Examiner*—Deborah C. Lambkin
(74) *Attorney, Agent, or Firm*—Nixon Peabody LLP

(57) ABSTRACT

Process for the synthesis of R(+)α-lipoic acid comprising the following stages: a) Salifying of racemic 6,8-halo-octanoic acid with S(–)α-methylbenzylamine; b) separation by filtration of the crystallized diastereoisomeric salt of R(+)6,8-di-halo-octanoic acid-S(–)α-methylbenzylamine; c) purification by re-crystallization of the diastereoisomeric salt of R(+)6,8-di-halo-octanoic acid-S(–)α-methylbenzylamine; (d) separation of the diastereoisomeric salt to obtain R(+)6,8-di-halo-octanoic acid by reation of said salt with strong mineral acids in an aqueous solution with a dilution between 2 and 10% by weight; e) esterification of R(+)6,8-di-halo-octanoic acid to obtain the corresponding alkyl ester; f) reaction of the alkyl ester of R(+) 6,8-di-halo-octanoic acid in an organic solvent with an aqueous solution of alkali disulfide in presence of a compound for phase transfer catalysis; g) hydolysis of the ester of R(+)α-lipoic acid.

31 Claims, No Drawings

SYNTHESIS OF R(+)α-LIPOIC ACID

FIELD OF THE INVENTION

The present invention relates to a process of synthesis of R(+)α-lipoic acid through the formation of diastereoisomeric salts of racemic 6,8-di-halooctanoic acid with optic isomers of α-methylbenzylamine, separation of R(+)-dihalooctanoic acid and its transformation into the corresponding α-lipoic acid with phase transfer catalysis.

STATE OF THE ART

It is well known from the state of the art the process of resolution of racemic mixtures, or racemates, i.e. the splitting of a racemate into the enantiomers constituting it. The racemate is first transformed into a mixture of diastereoisomers by reaction with an optically active substance. The diastereoisomers thus obtained, characterized by different physical properties among which solubility, are generally separated by fractioned crystallization. The enantiomers of the starting racemic mixture are obtained from said separated diastereoisomers by simple chemical reactions of separation of said diastereoisomers.

U.S. Pat. No. 5,281,722 describes diastereoisomeric salts obtained from pure enantiomers of α-lipoic acid by reaction with optic isomers of α-methylbenzylamine. Knows procedures describe methods for the preparation of said diastereoisomeric salts and their use as intermediate products in the resolution of a racemic mixture of thioctic acid in both optically active enantiomeric forms R(+) and S(−) of α-lipoic acid. The process of resolution of racemic thioctic acid has a low yield, in particular for the separation of the R(+)α-lipoic enantiomer (see Examples 7 and 8 of U.S. Pat. No. 5,281,722).

As a matter of fact, the purification processes described at the state of the art for diastereoisomeric salts have a low enantiomeric enrichment of the salt of the R(+)α-lipoic isomer. This is further confirmed by the high number of re-crystallizations carried out on diastereoisomeric salts before the scission reaction with acids.

Tests carried out by the Applicant show that the scission of the purified diastereoisomeric salts by addition of inorganic acids, for instance mineral acids such as 1N hydrochloric acid, to obtain the two separated optically active enantiomeric forms R(+) and S(−) of α-lipoic acid, as described in U.S. Pat. No. 5,281,722, results in low-quality enantiomers of α-lipoic acid (presence of polymers).

The state of the art describes the use of diastereoisomeric salts obtained from the enantiomers of α-lipoic acid by means of reaction with optically active bases in order to separate the isomers R(+) and S(−) of α-lipoic acid. However, the processes described at the state of the art, as verified by the Applicant, are characterized by complex and long methods for purifying intermediate diastereoisomeric salts, with low yields of resolution of racemates as well as an unsatisfying quality of the optic isomers thus obtained.

There was therefore a need for a process of synthesis of the optic isomer R(+) of α-lipoic acid which could represent an alternative to processes at the state of the art comprising as intermediate product of reaction racemic thioctic acid. In particular, there was a need for synthesis processes which could give a high quality and high purity optic isomer of α-lipoic acid with higher yields.

SUMMARY

It has now been found a new process of synthesis of R(+)α-lipoic acid through the resolution of racemic 6,8-di-halo-octanoic acid with the optically active base (S)-α-methylbenzylamine and the reaction with the alkali disulfide of the corresponding esterified enantiomer alkali R(+)6,8-di-halooctanoate by phase transfer catalysis, said process overcoming the disadvantages characterizing the processes at the state of the art, such as complexity, low yield and low quality of the obtained optic isomers.

Quite unexpectedly and surprisingly, the Applicant has found a new process of synthesis of R(+)α-lipoic acid by salification of 6,8-di-halo-octanoic acid with the optically active base S(−)α-methylbenzylamine to obtain the diastereoisomeric salt of (+)-6,8-di-halo-octanoic acid-S(−)α-methylbenzylamine, followed by its purification by fractioned crystallization and scission of the salt with acids, thus obtaining the enantiomer (+)-6,8-di-halooctanoic acid, which, after being esterified, is reacted by phase transfer catalysis with aqueous solutions of alkali disulfide in order to obtain esterified R(+)α-lipoic acid.

DETAILED DESCRIPTION OF THE INVENTION

An object of the present invention is therefore a process of synthesis of R(+)α-lipoic acid comprising the following stages:

a) salifying of racemic 6,8-halooctanoic acid with S(−)α-methylbenzylamine, wherein the molar ratio S(−)α-methylbenzylamine/racemic 6,8-di-halooctanoic acid is between 0.45 and 0.65;

b) separation by filtration of the crystallized diastereoisomeric salt of R(+)6,8-dihalo-octanoic acid-S(−)α-methylbenzylamine;

c) purification by re-crystallization of the diastereoisomeric salt of R(+)6,8-di-halooctanoic acid-S(−)α-methylbenzylamine;

d) separation of the diastereoisomeric salt to obtain R(+)6,8-di-halooctanoic acid by reaction of said salt with strong mineral acids in an aqueous solution with a dilution between 2 and 10% by weight;

e) esterification of R(+)6,8-di-halo-octanoic acid to obtain the corresponding alkyl ester;

f) reaction of the alkyl ester of R(+)6,8-di-halo-octanoic acid in an organic solvent with an aqueous solution of alkali disulfide in presence of a compound for phase transfer catalysis selected from the group consisting of quaternary ammonium or phosphonium salts having the following general formula:

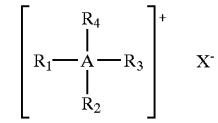

where:

A is nitrogen or phosphorus,

X is selected from the group consisting of Cl, Br, I, $HSO_4$ e $H_2PO_4$, and the substituents $R_1$, $R_2$, $R_3$ e $R_4$ are selected from the group consisting of linear or branched alkyl radicals having one to twenty carbon atoms ($C_1$–$C_{20}$), said substituents being identical or different one from the other, or only one of said substituents is selected from the group consisting of arylalkyl radicals having the following formula —$(CH_2)_nC_6H_5$ in which n=1–16;

g) hydrolysis of the ester of R(+)α-lipoic acid.

The halogen substituents of the racemic 6,8-di-halooctanoic acid, identical or different one from the other, are selected from the group consisting of Cl, Br or I.

Said racemic 6,8-di-halo-octanoic acid is preferably 6,8-dichlorooctanoic acid, a product which can be easily found on the market, produced according to the description contained in J.A.C.S. Volume 79, 1957, pages 6483–6487.

According to the process of synthesis described in the present invention, in salifying stage a) the molar ratio S(−)α-methylbenzylamine/racemic 6,8-di-halooctanoic acid is preferably between 0.48 and 0.60, still more preferably between 0.50 and 0.58. The salifying in stage a) is carried out at atmospheric pressure in an organic solvent, preferably ethyl acetate, at a temperature between 20 and 40° C., preferably between 25 and 30° C. The concentration of racemic 6,8-di-halooctanoic acid in salification stage a) is between 10 and 40% w/v, preferably between 15 and 35% w/v, still more preferably between 20 and 30% w/v of solvent.

Stage b), i.e. separation by filtration of the diastereoisomeric salt, takes place at a temperature of 0 to 10° C., preferably at 2° C.

In stage c), i.e. purification by recrystallization of the diastereoisomeric salt of R(+)6,8-di-halooctanoic acid-S(−)α-methylbenzylamine, the solvents used are alkyl esters of aliphatic or aromatic carboxylic acids, in which alkyl is $C_1$–$C_3$, preferably alkyl esters of aliphatic carboxylic acids having 2 to 4 carbon atoms, heating at a temperature between 40 and 65° C., preferably between 45 and 60° C., still more preferably between 50 and 55° C.

In stage d), i.e. separation of the diastereoisomeric salt, the aqueous mineral acid is preferably sulfuric acid with a dilution between 4 and 8% by weight, still more preferably sulfuric acid is diluted to 5% by weight.

Stage e), i.e. esterification of R(+)6,8-di-halo-octanoic acid, comprises a reaction of esterification according to methods well known in the field of esterification of aliphatic carboxylic acids with aliphatic or aromatic alcohols.

According to the present invention alkyl esters of R(+)6,8-di-halo-octanoic acid are linear or branched $C_1$–$C_6$ esters, preferably linear or branched $C_1$–$C_3$ esters, still more preferably methyl ester and ethyl ester.

According to the present invention the amount of alkyl esters of R(+)6,8-di-halo-octanoic acid in the reaction taking place in stage f) is between 5 and 60% by weight, preferably between 10 to 40% by weight, still more preferably between 15 to 30% by weigh with respect to the organic solvent.

The organic solvent used in the reaction taking place in stage f) is a solvent which cannot be mixed with water, selected from the group consisting of: linear or branched aliphatic $C_5$–$C_{10}$ hydrocarbons, or aromatic $C_5$–$C_{10}$ hydrocarbons also having substituting groups selected from the group consisting of halogen, nitro or nitrile groups; esters of aliphatic or aromatic carboxylic acids; linear or cyclic ethers, linear or cyclic $C_4$–$C_{10}$ ketones; carbon disulfide; carbon tetrachloride. The solvent is preferably benzene or toluene.

The process for the synthesis of R(+)α-lipoic acid according to present invention comprises the phase transfer of the disulfide ion from the aqueous solution containing the corresponding alkali disulfide to the organic phase which cannot be mixed with water, containing the alkyl ester of R(+)6,8-di-halo-octanoic acid. The aqueous solution of alkali disulfide can be prepared by reacting in water sulfur (S) with the corresponding alkali sulfide.

Preferred alkali disulfides are sodium disulfide ($Na_2S_2$) and potassium disulfide ($K_2S_2$) or their mixtures, still more preferred sodium disulfide.

In the reaction taking place in stage f) of the process of synthesis of R(+)α-lipoic acid according to the present invention, the molar ratio alkali disulfide/alkyl ester of R(+)6,8-di-halo-octanoic acid is between 0.8 and 1.2, preferably between 0.9 and 1.1, still more preferably between 0.95 and 1.0.

The preferred compounds for phase transfer catalysis used for the synthesis of R(+)α-lipoic acid which is the object of the present invention, are selected from the group consisting of tetrabutylammonium bromide, tetrabutylphosphonium bromide, methyltrioctylammonium chloride (ALIQUAT® 336), methyl-($C_8$–$C_{10}$)-trialkylammonium chloride (ADOGEN® 464) and tetrabutylammonium hydrogensulfate; still more preferred are tetrabutylammonium bromide and tetrabutylammonium hydrogensulfate.

According to the process of synthesis described in the present invention, in the reaction taking place in stage f) the compound for phase transfer catalysis, a quaternary salt, is present in an amount between 0.5 to 10% in moles, preferably between 1 to 5% in moles, still more preferably between 2 and 4% in moles with respect to the alkyl ester of 6,8-di-halo-octanoic acid.

The temperature of the reaction taking place in stage f) is between 20 and 130° C., preferably between 60 and 100° C., still more preferably between 80 and 90° C. Stage g), i.e. hydrolysis of the ester of R(+)α-lipoic acid, is a hydrolysis with alkali/alcaline-earth hydroxides in presence of organic solvents, such as alcohols and polyols, ethers and hydroxy ethers, ketones and hydroxy ketones, which can be mixed with water in a volume ratio of 50:50 to 95:5 at a temperature between 0 and 100° C. The concentration of the ester with respect to the organic solvent is between 5 and 50% w/v and the molar ratio ester/hydroxide is between 0.5 and 1. Free R(+)α-lipoic acid can be recovered by treatment with aqueous mineral acids diluted 1 to 20% by weight or water-soluble organic acids.

Reaction products and intermediate products are characterized with $^1$H-NMR, Mass and HPLC analyses.

The following area some examples disclosing though not limiting the present invention.

EXAMPLE 1 a) 40 g (0.187 moles) of racemic 6,8-dichlorooctanoic acid are dissolved in 150 ml of ethyl acetate at 25–30° C. This solution is added with 12.3 g (0.101 moles) of S(−)α-methylbenzylamine. Said solution is cooled down first at 18–20° C. until the precipitation starts, and then at 0–5° C. The solid obtained is filtered, washed with ethyl acetate (10 ml), thus obtaining 15.3 g of humid salt of (+)-6,8-dichlorooctanoic acid-S(−)α-methylbenzylamine.

b) The mother liquors resulting from the crystallization taking place in stage a) are extracted with 100 ml of sulfuric acid at 5% by weight, checking that the pH value of the aqueous phase is 1. The organic phase is washed twice with 20 ml of water, then concentrated by solvent distillation at atmospheric pressure until reaching a volume of 130–140 ml. The solution is added with 9.75 g (0.08 moles) of R(+)α-methylbenzylamine, cooled down first at 18–20° C. until the precipitation starts, and then at 0–5° C. The solid is filtered and washed with 10 ml of ethyl acetate, thus obtaining 8.2 g of humid salt of (−)-6,8-dichlorooctanoic acid-R(+)α-methylbenzylamine.

c) The mothers liquors resulting from the crystallization taking place in stage b) are extracted with 50 ml of sulfuric acid 5% by weight, checking that the pH value of the aqueous phase is ≦1. The organic phase is washed twice with 20 ml of water, then concentrated by solvent distillation at atmospheric pressure until reaching a volume of 40–45 ml. The solution is added with 50 ml of ethyl acetate and 9.8 g (0.081 moles) of S(−)α-methylbenzylamine, cooled down first at 18–20° C. until the precipitation starts, and then at 0–5° C. The solid is filtered and washed with 10 ml of ethyl acetate, thus obtaining 12 g of humid salt of (+)-6,8-dichlorooctanoic acid-S(−)α-methylbenzylamine.

d) The humid salts of (+)-6,8-dichlorooctanoic acid-S(−) α-methylbenzylamine obtained in stages a) and c) are united and crystallized two times, each time with 55 ml of ethyl acetate. 16 g of humid product are obtained and dried under vacuum, thus obtaining 13.5 g of the salt of (+)-6,8-dichlorooctanoic acid-S(−)α-methylbenzylamine. Said salt is suspended in a mixture of water (60 ml) and toluene (60 ml) and acidified with sulfuric acid at 5% by weight until pH=1. The organic phase is separated and concentrated under vacuum, thus obtaining 9 g of (+)-6,8-dichlorooctanoic acid (yield=45%).

$[\alpha]^{24}_D = 26.7$ (c=2, ethanol).

EXAMPLE 2

9 g (0.042 moles) of (+)-6,8-dichlorooctanoic acid are dissolved in 120 ml of methanol containing 0.45 ml of aqueous hydrochloric acid at 37% by weight. The solution is refluxed for two hours, the solvent is evaporated at reduced pressure, 17 ml of toluene are added and the obtained solution is washed twice with 10 ml of water. The toluene phase is concentrated under vacuum, thus obtaining 9.4 g of methyl (+)-6,8-dichlorooctanoate (yield=98.6%).

$[\alpha]^{20}_D = 26.5$ (c=1, toluene).

EXAMPLE 3

A mixture consisting of 5.65 g (0.043 moles) of sodium sulfide 60% by weight, 1.18 g (0.037 moles) of sulfur and 20 ml of water is heated at 85° C. for 30 minutes. After being filtered to remove the insoluble portion, the solution is added in three hours to a solution consisting of 9.4 (0.041 moles) of methyl (+)-6,8-dichlorooctanoate, 0.37 g (0.0011 moles) of tetrabutylammonium bromide and 18.5 ml of toluene, kept at 82° C. The mixture is refluxed (90° C.) for 1 hour and cooled down at 30° C., the organic phase is separated and washed with 5 ml of water. The whole is concentrated under vacuum, thus obtaining 8.6 g of methyl ester of R(+)α-lipoic acid (yield=94.4%).

The final product is characterized by means of $^1$H-NMR and Mass analyses:

$^1$H-NMR—δ (300 MHz, CDCl$_3$): 1.4 (2H, m); 1.67 (4H, m); 1.83 (1H, td); 2.24 (2H, t); 2.4 (1 H, td); 3.1 (2H, m); 3.5 (1H, m); 3.66 (3H, s).

Mass (EI): 220 (M$^+$); 189 (—CH$_3$O).

$[\alpha]^{20}_D = 88$ (c=1.8 toluene).

EXAMPLE 4

8.6 g (0.039 moles) of methyl ester of R(+)α-lipoic acid are added to a solution consisting of 2.36 g (0.042 moles) of potassium hydroxide at 90% by weight, 19 ml of methanol and 3.8 ml of water. The mixture obtained is heated at 50° C. for 2 hours, cooled down at 30° C. and added with 40 ml of toluene. The whole is acidified with phosphoric acid 10% by weight, keeping temperature below 30° C. The organic phase is separated and washed three times, each time with 10 ml of an aqueous solution of sodium chloride at 10% by weight. The solution is de-hydrated on sodium sulfate and concentrated to dryness by solvent evaporation under vacuum. 3.3 ml of ethyl acetate and 41 ml of cyclohexane are added, the solution is heated at 40° C. and treated with decolorizing carbon, and the clear solution obtained is slowly cooled down at 0° C. The solid is filtered and washed with 5 ml of cyclohexane, thus obtaining 3.6 g of R(+)α-lipoic acid (yield=45%).

$[\alpha]^{20}_D = 119.1$ (c=1, ethanol).

e.e.>99% (HPLC).

What is claimed is:

1. Process for the synthesis of R(+)α-lipoic acid comprising the following stages:
    a) Salifying of racemic 6,8-halo-octanoic acid with S(−) α-methylbenzylamine, in which the molar ratio S(−)α-methylbenzylamine/racemic 6,8-di-halo-octanoic acid is between 0.45 and 0.65;
    b) separation by filtration of the crystallized diastereoisomeric salt of R(+)6,8-di-halo-octanoic acid-S(−)α-methylbenzylamine;
    c) purification by re-crystallization of the diastereoisomeric salt of R(+)6,8-di-halo-octanoic acid-S(−)α-methylbenzylamine;
    d) separation of the diastereoisomeric salt to obtain R(+) 6,8-di-halo-octanoic acid by reaction of said salt with strong mineral acids in an aqueous solution with a dilution between 2 and 10% by weight;
    e) esterification of R(+)6,8-di-halo-octanoic acid to obtain the corresponding alkyl ester;
    f) reaction of the alkyl ester of R(+)6,8-di-halo-octanoic acid in an organic solvent with an aqueous solution of alkali disulfide in presence of a compound for phase transfer catalysis selected from the group consisting of quaternary ammonium or phosphonium salts having the following general formula:

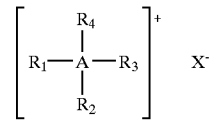

where:

A is nitrogen or phosphorus,

X is selected from the group consisting of Cl, Br, I, HSO$_4$ e H$_2$PO$_4$, and the substituents R$_1$, R$_2$, R$_3$ e R$_4$ are selected from the group consisting of linear or branched alkyl radicals having one to twenty carbon atoms (C$_1$–C$_{20}$), said substituents being identical or different one from the other, or only one of said substituents is selected from the group consisting of arylalkyl radicals having the following formula —(CH$_2$)$_n$C$_6$H$_5$ in which n=1–16;

g) hydrolysis of the ester of R(+)α-lipoic acid.

2. Process according to claim 1, wherein said halogen substituents of racemic 6,8-di-halo-octanoic acid, identical or different one from the other, are selected from the group consisting of Cl, Br or I.

3. Process according to claim 2, wherein the racemic 6,8-di-halo-octanoic acid is 6,8-dichloroctanoic acid.

4. Process according to claim 1, wherein in salifying stage a) the molar ratio S(−)α-methylbenzylamine/racemic 6,8-di-halo-octanoic acid is between 0.48 and 0.60.

5. Process according to claim 4, wherein the molar ratio S(−)α-methylbenzylamine/racemic 6,8-di-halo-octanoic acid is between 0.50 and 0.58.

6. Process according to claim 1, wherein the concentration of racemic 6,8-di-halo-octanoic acid in salifying stage a) is between 10 and 40% w/v of solvent.

7. Process according to claim 6, wherein the concentration of racemic 6,8-di-halo-octanoic acid is between 15 and 35% w/v of solvent.

8. Process according to claim 7, wherein the concentration of racemic 6,8-di-halo-octanoic acid is between 20 and 30% w/v of solvent.

9. Process according to claim 1, wherein in stage d), i.e. separation of the diastereoisomeric salt, the aqueous mineral acid is sulfuric acid with a dilution between 4 and 8% by weight.

10. Process according to claim 9, wherein sulfuric acid is diluted to 5% by weight.

11. Process according to claim 1, wherein said alkyl esters of R(+)6,8-di-halo-octanoic acid are linear or branched $C_1$–$C_6$ esters.

12. Process according to claim 11, wherein said alkyl esters of R(+)6,8-di-halo-octanoic acid are linear or branched $C_1$–$C_3$ esters.

13. Process according to claim 12, wherein said alkyl esters of R(+)6,8-di-halo-octanoic acid are methyl ester or ethyl ester.

14. Process according to claim 1, wherein the amount of alkyl esters of R(+)6,8-di-halo-octanoic acid in the reaction taking place in stage f) is between 5 and 60% by weight with respect to the organic solvent.

15. Process according to claim 14, wherein the amount of alkyl esters of R(+)6,8-di-halo-octanoic acid is between 10 and 40% by weight with respect to the organic solvent.

16. Process according to claim 15, wherein the amount of alkyl esters of R(+)6,8-di-halo-octanoic acid is between 15 and 30% by weight with respect to the organic solvent.

17. Process according to claim 1, wherein the organic solvent used in the reaction taking place in stage f) is a solvent which cannot be mixed with water, selected from the group consisting of: linear or branched aliphatic $C_5$–$C_{10}$ hydrocarbons, or aromatic $C_5$–$C_{10}$ hydrocarbons also having substituting groups selected from the group halogen, nitro or nitrile groups, esters of aliphatic or aromatic carboxylic acids; linear or cyclic ethers; linear or cyclic $C_4$–$C_{10}$ ketones; carbon disulfide; carbon tetrachloride.

18. Process according to claim 17, wherein said solvent is benzene or toluene.

19. Process according to claim 1, wherein the alkali disulfides are sodium disulfide ($Na_2S_2$) or potassium disulfide ($K_2S_2$) or their mixtures.

20. Process according to claim 19, wherein said alkali disulfide is sodium disulfide.

21. Process according to claim 1, wherein in the reaction taking place in stage f) the molar ratio alkali disulfide/alkyl ester of R(+)6,8-di-halo-octanoic acid is between 0.8 and 1.2.

22. Process according to claim 21, wherein said molar ratio is between 0.9 and 1.1.

23. Process according to claim 22, wherein said molar ratio is between 0.95 and 1.0.

24. Process according to claim 1, wherein the quaternary ammonium or phosphonium salts are selected from the group consisting of tetrabutylammonium bromide, tetrabutylphosphonium bromide, methyltrioctylammonium chloride (ALIQUAT® 336), methyl-($C_8$–$C_{10}$)-trialkylammonium chloride (ADOGEN® 464) and tetrabutylammonium hydrogensulfate.

25. Process according to claim 24, wherein said quaternary salts are tetrabutylammonium bromide or tetrabutylammonium hydrogensulfate.

26. Process according to claim 1, wherein the quaternary ammonium or phosphonium salt is present in an amount of 0.5 to 10% in moles with respect to the alkyl ester of 6,8-di-halo-octanoic acid.

27. Process according to claim 26, wherein said quaternary salt is present in an amount of 1 to 5% in moles with respect to the alkyl ester of 6,8-di-halo-octanoic acid.

28. Process according to claim 27, wherein said quaternary salt is present in an amount of 2 to 4% in moles with respect to the alkyl ester of 6,8-di-halo-octanoic acid.

29. Process according to claim 1, wherein the temperature of the reaction taking place in stage f) is between 20 and 130° C.

30. Process according to claim 29, wherein said temperature is between 60 and 100° C.

31. Process according to claim 30, wherein said temperature is between 80 and 90° C.

* * * * *